US009724340B2

(12) United States Patent
Liang et al.

(10) Patent No.: US 9,724,340 B2
(45) Date of Patent: Aug. 8, 2017

(54) ANTITUSSIVE COMPOSITIONS AND METHODS (71) Applicant: Attenua, Inc., New York, NY (US)

(72) Inventors: Jing Liang, New York, NY (US); Peter Dicpinigaitis, Armonk, NY (US); Brendan Canning, Baltimore, MD (US); Robert Devita, Westfield, NJ (US)

(73) Assignee: Attenua, Inc., New York, NY (US)

( * ) Notice: Subject to any disclaimer, the term of this patent is extended or adjusted under 35 U.S.C. 154(b) by 0 days.

(21) Appl. No.: 15/208,266

(22) Filed: Jul. 12, 2016

(65) Prior Publication Data

US 2017/0027918 A1   Feb. 2, 2017

Related U.S. Application Data (60) Provisional application No. 62/199,353, filed on Jul. 31, 2015.

(51) Int. Cl.
*A61K 31/439* (2006.01)
*A61K 31/444* (2006.01)
*A61K 45/06* (2006.01)
*A61K 9/00* (2006.01)

(52) U.S. Cl.
CPC .......... *A61K 31/444* (2013.01); *A61K 31/439* (2013.01); *A61K 45/06* (2013.01); *A61K 9/0073* (2013.01)

(58) Field of Classification Search
None
See application file for complete search history.

(56) References Cited

U.S. PATENT DOCUMENTS

| | | |
|---|---|---|
| 4,203,990 A | 5/1980 | Yen |
| 4,922,901 A | 5/1990 | Brooks |
| 4,970,315 A | 11/1990 | Schmidhalter |
| 5,212,188 A | 5/1993 | Caldwell |
| 5,217,975 A | 6/1993 | Wadsworth |
| 5,219,849 A | 6/1993 | Lotti |
| 5,276,043 A | 1/1994 | Lippiello |
| 5,346,906 A | 9/1994 | Baker |
| 5,510,355 A | 4/1996 | Bencherif |
| 5,583,140 A | 12/1996 | Bencherif |
| 5,597,919 A | 1/1997 | Dull |
| 5,604,231 A | 2/1997 | Smith |
| 5,616,707 A | 4/1997 | Crooks |
| 5,616,716 A | 4/1997 | Dull |
| 5,663,356 A | 9/1997 | Ruecroft |
| 5,712,270 A | 1/1998 | Sabb |
| 5,811,442 A | 9/1998 | Bencherif |
| 5,824,692 A | 10/1998 | Lippiello |
| 5,852,041 A | 12/1998 | Cosford |
| 5,853,696 A | 12/1998 | Elmaleh |
| 5,859,004 A | 1/1999 | Olesen |
| 5,861,423 A | 1/1999 | Caldwell |
| 5,952,339 A | 9/1999 | Bencherif |
| 5,969,144 A | 10/1999 | London |
| 6,432,975 B1 | 8/2002 | Schmitt |
| 6,734,215 B2 | 5/2004 | Shytle |
| 6,953,855 B2 | 10/2005 | Mazurov et al. |
| 7,115,629 B2 | 10/2006 | Farrerons |
| 7,425,561 B2 | 9/2008 | Mazurov et al. |
| 7,754,189 B2 | 7/2010 | Mazurov et al. |
| 7,767,193 B2 | 8/2010 | Mazurov et al. |
| 7,981,906 B2 | 7/2011 | Dull et al. |
| 8,084,462 B2 | 12/2011 | Mazurov et al. |
| 8,119,659 B2 | 2/2012 | Dull et al. |
| 8,124,618 B2 | 2/2012 | Mazurov et al. |
| 8,124,619 B2 | 2/2012 | Mazurov et al. |
| 8,143,272 B2 | 3/2012 | Mazurov et al. |
| 8,158,649 B2 | 4/2012 | Mazurov et al. |
| 8,476,296 B2 | 7/2013 | Bencherif et al. |
| 8,541,446 B2 | 9/2013 | Bencherif et al. |
| 8,541,447 B2 | 9/2013 | Mazurov et al. |
| 8,846,715 B2 | 9/2014 | Bencherif et al. |
| 8,901,151 B2 | 12/2014 | Bencherif et al. |
| 9,173,876 B2 | 11/2015 | Bencherif et al. |
| 2005/0255040 A1 | 11/2005 | Mazurov |
| 2008/0003280 A1 | 1/2008 | Levine |
| 2008/0138287 A1 | 6/2008 | Mazurov |
| 2015/0045386 A1 | 2/2015 | Bencherif |

FOREIGN PATENT DOCUMENTS

| | | |
|---|---|---|
| IN | 173570 B | 6/1994 |
| WO | 9112254 A1 | 8/1991 |
| WO | 9408992 A1 | 4/1994 |
| WO | 9503306 A1 | 2/1995 |
| WO | 9612711 A1 | 5/1996 |
| WO | 9631475 A2 | 10/1996 |
| WO | 9640682 A1 | 12/1996 |
| WO | 9701556 A1 | 1/1997 |

(Continued)

OTHER PUBLICATIONS

Dicpinigaitis, P., Cough Reflex Sensitivity in Cigarette Smokers, Chest 123, 685-688, 2003.
Dicpinigaitis, P. et al., Effect of Smoking Cessation on Cough Reflex Sensitivity, Eur Respir J 28, 786-790, 2006.
Dicpinigaitis, P. et al., Effect of e-Cigarette Use on Cough Reflex Sensitivity, Chest 149(1), 161-165, 2016.
Papke, R. et al., The Analgesic-Like Properties of the Alpha7 nAChR Silent Agonist NS6740 is Associated with Non-Conducting Conformations of the Receptor, Neuropharmacology, Apr. 1-25, 2015.
Arneric, S. et al., Cholinergic Channel Modulators as a Novel Therapeutic Strategy for Alzheimer's Disease, Exp Opin Invest Drugs 5(1), 79-100, 1996.

(Continued)

*Primary Examiner* — Jeffrey S Lundgren
*Assistant Examiner* — Meghan Finn
(74) *Attorney, Agent, or Firm* — Dennis A. Bennett; Brock Levin (57) ABSTRACT

Disclosed herein are compositions which include nicotinic receptor agonists, specifically of the α7 nAChR subtype, and methods for suppressing cough.

20 Claims, 4 Drawing Sheets

(56) References Cited

FOREIGN PATENT DOCUMENTS

| | | |
|---|---|---|
| WO | 9711072 A1 | 3/1997 |
| WO | 9730998 A1 | 8/1997 |
| WO | 9825619 A1 | 6/1998 |
| WO | 9854181 A1 | 12/1998 |
| WO | 9903859 A1 | 1/1999 |
| WO | 9951602 A1 | 10/1999 |
| WO | 9962505 A2 | 12/1999 |
| WO | 0034276 A1 | 6/2000 |
| WO | 0136417 A1 | 5/2001 |
| WO | 0185727 A1 | 11/2001 |
| WO | 0215662 A2 | 2/2002 |
| WO | 0216356 A2 | 2/2002 |
| WO | 0216357 A2 | 2/2002 |
| WO | 0216358 A2 | 2/2002 |
| WO | 0217358 A2 | 2/2002 |
| WO | 02051841 A1 | 7/2002 |
| WO | 2004076449 A2 | 9/2004 |

OTHER PUBLICATIONS

Arneric, S. et al., Preclinical Pharmacology of ABT-418: A Prototypical Cholinergic Channel Activator for the Potential Treatment of Alzheimer's Disease, CNS Drug Rev 1(1), 1-26, 1995.
Astles, PC et al., Recent Progress in the Development of Subtype Selective Nicotinic Acetylcholine Receptor Ligands, Current Drug Targets—CNS & Neurological Disorders 1(4), 337-348, 2002.
Bannon, AW et al., Broad-Spectrum, Non-Opioid Analgesic Activity by Selective Modulation of Neuronal Nicotinic Acetylcholine Receptors, Science 279, 77-80, 1998.
Barnes, P., Nuclear Factor_kB, Int J Biochem Cell Biol 29(6), 867-870, 1997.
Bencherif, M. et al., RJR-2403: A Nicotinic Agonist with CNS Selectivity I. In Vitro Characterization, JPET 279(3), 1413-1421, 1996.
Birtwistle, J., The Role of Cigarettes and Nicotine in the Onset and Treatment of Ulcerative Colitis, Postgrad Med J 72, 714-718, 1996.
CAS Printout for Begue et al., Dec. 1969.
CAS Printout for IN 173 570, 54-25, Jun. 4, 1994.
CAS Printout for Schmidhalter et al., Nov. 1990.
Chiari, A. et al., Sex Differences in Cholinergic Analgesia I: A Supplemental Nicotinic Mechanism in Normal Females, Anesthesiology 91 (5), 1447-1454, 1999.
Damaj, MI et al., Antiniciceptive and Pharmacological Effects of Metanicotine, a Selective Nicotinic Agonist, JPET 291 (1), 390-398, 1999.
Dolle, F. F et al., Synthesis and Preliminary Evaluation of a Carbon-11-labelled Agonist of the a-7 Nicotinic Acetylcholine Receptor, J Labelled Comp Radiopharm 44, 785-795, 2001.
Dunlop, J., et al., 'In vitro screening strategies for nicotinic receptor ligands,' Biochemical Pharmacology, 74: 1172-1181 (2007).
Ebadi, M. et al., Neurotrophins and Their Receptors in Nerve Injury and Repair, Neurochem Int 30(4/5), 347-374, 1997.
Ennaceur, A. et al., A New One-Trial Test for Neurobiological Studies of Memory in Rats. II: Effects of Piracetam and Pramiracetam, Behavioural Brain Research 33, 197-207, 1988.
EP Search Report for EP Application No. 11194161 mailed May 23, 2012.
Evans, EA et al., Isotopic Labeling with Carbon-14 and Tritium, Principles of Radiopharmacology, 11-13, 1992.
Freedman, R., et al., 'Linkage of a neurophysiological deficit in schizophrenia to a chromosome 15 locus,' Proc. Natl. Acad. Sci., 94: 587-592 (1997).
Gavezzotti, Are Crystal Structures Predictable?, Accounts of Chemical Research, vol. 27, pp. 309-314 (1994).
Hanisch, Uwe-Karsten et al., 'Modulation of Hippocampal Acetylcholine Release: A Potent Central Action of Interleukin-2,' the Journal of Neuroscience, vol. 13 (8), pp. 3368-3374 (1993).
Hauser TA, Kucinski A, Jordan KG, Gatto GG, Wersinger SR, Hesse RZ, Stachowiak EK, Stachowiak MK, Lippiello PM, Bencherif M. TC-5619: An alpha7 neuronal nicotinic receptor-selective agonist that ameliorates positive and negative symptoms and enhances cognitive function in animal models of schizophrenia. Biochem. Phamacol, Oct. 1, 2009; 78 (7), 803-12.
Heeschen, C. et al., A Novel Angiogenic Pathway Mediated by Non-Neuronal Nicotinic Acetylcholine Receptors, J Clin Invest 110(4), 527-536, 2002.
Holladay, M.W. et al.: 'Neuronal Nicotinic Acetylcholine Receptros as Targets for Drug Discovery' J. Med. Chem., vol. 40, No. 26, Dec. 19, 1997 (Dec. 12, 1997), pp. 4169-4194, XP002124847 Washington.
Hoyer, D. et al., Partial Agonists, Full Agonists, Antagonists: Dilemmas of Definition, TiPS Reviews 14(7), 270-275, 1993.
International Search Report, PCT/US99119906, Jan. 13, 2000.
Jeyarasasingam, G., et al., 'Stimulation of Non-a7 Nicotinic Receptors Partially Protects Dopaminergic Neurons from 1-Methyl-4 Phenylpyridinium-Induced Toxicity in Culture,' Neuroscience 109(2), 275-285 (2002).
Jonakait, G. Miller, TINS, 'Neural-immune interactions in sympathetic ganglia,' vol. 16, No. 10, pp. 419-423 (1993).
Kaiser, S. et al., a-Bungarotoxin-Sensitive Nicotinic Receptors Indirectly Modulate [3H] Dopamine Release in Rat Striatal Slices Via Glutamate Release, Molecular Pharmacology 58, 312-318, 2000.
Kalamida, et al. (FEBS Journal, 274 (2007), 3799-3845).
Lavand'Homme, P. et al., Sex Differences in Cholinergic Analgesia II: Differing Mechanisms in Two Models of Allodynia, Anesthesiology 91 (5), 1455-1461, 1999.
Leonard, S. et al., Nicotinic Receptor Function in Schizophrenia, Schizophrenia Bulletin 22(3), 431-445, 1996.
Levin, ED et al., AR-R17779, an a7 nicotinic agonist, improves learning and memory in rats, Behavioural Pharamacology 10(6/7), 675-680, 1999.
Levin, ED et al., Nicotinic Treatment for Cognitive Dysfunction, Current Drug Targets—CNS and Neurological Disorders 1(4), 423-431, 2002.
Lippiello, P.M., et al., 'RJR-2403: A Nicotinic Agonist with CNS Selectivity II. In Vivo Characterization,' J. Pharmacol. Exp. Ther, 279(3): 1422-1429 (1996).
Macor, J. et al., The 5-HT3 Antagonist Tropisetron (ICS 205-930) is a Potent and Selective a7 Nicotinic Receptor Partial Agonist, Bioorg Med Chem Lett 11, 319-321, 2001.
Madretsma, G.S., et al., 'Nicotine inhibits the in vitro production of interleukin 2 and tumour necrosis factor-.alpha. by human monoclear cells,' Immunopharmacology, 35, pp. 47-51 (1996).
Madretsma, Stanley et al., 'In-vivo effect of nicotine on cytokine production by human non-adherent mononuclear cells,' European Journal of Gastroenterology & Hepatology, vol. 8, No. 10, pp. 1017-1020 (1996).
Marrero M, Lucas R, Salet C, Hauser TA, Mazarov A, Lippiello PM, Bencherif M. An Alpha 7Receptor-Selective Agonist Reduces Weight Gain and Metabolic Changes in a Mouse Model of Diabetes. J Pharmacol Exper Ther Fast Forward Sep. 28, 2009; e-pub.
Matthys, Patrick PhD. et al., 'Cytokines and Cachexia,' Nutrition, vol. 13, No. 9, pp. 763-770 (1997).
Mazurov, A. et al., Selective a7 Nicotinic Acetylcholine Receptor Ligands, Curr Med Chem 13(13), 1567-1584, 2006.
O'Neill et al., The Role of Neuronal Nicotinic Acetylcholine Receptors in Acute and Chronic Neurodegeneration, Curr Drug Targets CNS Neural Disord., Aug. 2000, 1(4), 399-411.
O'Neill, MJ et al., The Role of Neuronal Nicotinic Acetylcholine Receptors in Acute and Chronic Neurodegeneration, Current Drug Targets—CNS & Neurological Disorders 1(4), 399-411, 2002.
Olesen, PH et al., Identification of Novel (Isoxazole)Methylene-1-Azabicyclic Compounds with High Affinity for the Central Nicotinic Cholinergic Receptor, Bioorganic & Medicinal Chemistry Letters 7(15), 1963-1968, 1997.
Papke, R.L, and J.K.P. Papke, 'Comparative pharmacology of rat and human a7 nAChR conducted with net charge analysis,' Brit. J. Pharmacol., 137:49-61 (2002).
PCT/US2004/005044, International Search Report, Nov. 3, 2004.

(56) References Cited

OTHER PUBLICATIONS

Peacock, Mark E. et al., 'The Effect of Nicotine on Reproduction and Attachment of Human Gingival Fibroblasts in vitro,' J. Periodontal, vol. 64, No. 7, pp. 658-665 (1993).
Placzek, A.N., et al., 'An a7 Nicotinic Acetylcholine Receptor Gain-of-Function Mutant that Retains Pharmacological Fidelity,' Molecular Pharmacology, 68(6): 1863- 1876 (2005).
Poliacek et al., "Central Administration of Nicotine Suppresses Tracheobronchial Cough in Anesthetized Cats," Journal of Applied Psysiol, vol. 118, pp. 265-272, first published Dec. 4, 2014.
Pullan, Robert D. et al., 'Transdermal Nicotine for Active Ulcerative Colitis,' The New England Journal of Medicine, vol. 330, No. 12, pp. 811-815 (1994).
Pullan, Rupert D., 'Colonic mucus, smoking and ulcerative colitis,' Ann R. Coll. Surg Engl., 78, pp. 85-91 (1996).
Roux, S., et al., 'Models for Assessing Antipsychotics: Antagonism of Amphetamine-Induced Hyperactivity and Sterotypies in Mice,' Curr. Protocols in Pharmacol., Unit 5.17.1 (1999).
Salamone, et al. (McGill J. Med., 2000, 5:90-9).
Sandborn, W. J. et al., 'Nicotine tartrate liquid enemas for mildly to moderately active left-sided ulcerative colitis unresponsive to first-line therapy: a pilot study,' Ailment Pharmacol. Ther., 11, pp. 663-671 (1997).
Sartor, R. Balfour M.D., 'Pathogenesis and Immune Mechanisms of Chronic Inflammatory Bowel Diseases,' The American Journal of Gastroenterology, vol. 92, No. 12, pp. 5S-11S (1997).
Schmitt, J., 'Exploring the Nature of Molecular Recognition in Nicotinic Acetylcholine Receptors,' Cuff. Med. Chem., 7 (8): 749-800 (Aug. 2000).
Sharma, T. and L. Antonova, 'Cognitive function in schizophrenia: Deficits, functional consequences, and future treatment,' Psychiatr,. Clin. N. Am., 26: 25-40 (2003).
Shimohama, S. et al., Nicotinic Receptor—Mediated Protection Against B-Amyloid Neurotoxicity, Society of Biological Psychiatry 49, 233-239, 2001.
Shytle, R. et al., Cholinergic Modulation of Microglial Activation by a7 Nicotinic Receptors, Journal of Neurochemistry 89, 337-343, 2004.
Silverstein, Marc D., M.D. et al., 'Cigarette Smoking and Ulcerative Colitis: a Case-Control Study', Mayo Clin. Proc., vol. 69. pp. 425-429 (1994).
Snoek et al. (Br J Pharmacol. May 2010; 160(2): 322-333).
Stevens, K.E., et al., 'Selective a-.sub.7-nicotinic agonists normalize inhibition of auditory response in DBA mice,' Psychopharm. 136: 320-327 (1998).
Suemaru, K., et al., Nicotine blocks apomorphine-induced disruption of prepulse inhibition of the acoustic startle in rats: possible involvement of central nicotinic a7 receptors, British I of Pharmacology, 142(5): 843-850 (2004).
Tracey, Kevin J., 'The Inflammatory Reflex,' Nature, vol. 420, pp. 853-859 (Dec. 2002).
Utsugisawa, K., et al., 'Over-expression of a7 nicotinic acetylcholine receptor induces sustained ERK phosphorylation and N-cadherin expression in PC12cells,' Molecular Brain Research, 106: 88-93 (2002).
Van Dijk, Jeanette P.M. et al., 'Nicotine inhibits cytokine synthesis by mouse colonic mucosa,' European Journal of Pharmacology, 278, R11-R12 (1995).
Villemagne, V. et al., Nicotine and Related Compounds as PET and SPECT Ligands, Neuronal Nicotinic Receptors: Pharmacology and Therapeutic Opportunities, 235-250, 1999.
Vippagunta et al, 'Crystalline Solids', Advanced Drug Delivery Reviews, vol. 48, pp. 3-26 (2001).
Vitti, G., et al., 'Synthesis of a Benzo[b]-1,5,-naphtyridine Derivative as a Potential Constrained Nk.sub.1 Receptor Antagonist,' Tetrahedron Letters, 35(32): 5939-5942 (1994).
Wallace, John L. et al., 'Inflammatory Mediators in Gastrointestinal Defense and Injury,' Proc. Soc. Exp. Biol. Med., vol. 214, pp. 192-203 (1997).
Wang, H. et al., Nicotinic Acetylcholine Receptor a7 Subunit is an Essential Regulator of Inflammation, Nature, advance online publication, 1-4, Dec. 22, 2002.
Warawa, E.J., and N. J. Mueller, 'Quinuclidine Chemistry. 4.sup.1 Diuretic Properties of cis-3-Amino-2-benzhydrylquinuclidine,' Journal of Medicinal Chemistry, 18(6): 587-593 (1975).
Williams, M. et al., Neuronal Nicotinic Acetylcholine Receptors, Drug News Perspec 7(4), 205-223, 1994.
Wu, J., et al., 'Roles of nicotinic acetylcholine receptors 13subunits in function of human a4-containing nicotinic receptors,' J. Physiol. 576.1: 103-118 (2006).
Xiao et al., Proc. Nat. Acad Sci. (US, (2002), vol. 99, No. 12, p. 8360.
Yanina et al, Khim.-Karm, vol. 21(7), pp. 808-811 (1987).
Zijlstra, F. J. et al., 'Effect of nicotine on rectal mucus and mucosal eicosanoids,' Gut, 35, pp. 247-251 (1994).
PCT/US2016/044529, International Search Report and Written Opinion, dated Sep. 27, 2016, 12 pages.
American Psychiatric Association:, Diagnostic and Statistical Manual of Mental Disorders, Fourth Edition.
Freedman et al., Evidence in postmortem brain tissue for decreased number of hippocampal nicotinic receptors in schizophrenia, Biological Psychiatry, (1995), vol. 38, No. 1, p. 22-33.
International Search Report (PCT/US2008/071872, dated Feb. 11, 2010).
Mazuroy et al., 2-(Arylmethyl)-3-substituted Quinuclidines as Selective A7 Nicotinic Receptor Ligands, Bioorganic & Medicinal Chemistry Letters, Pergamon, Elsevier Science, vol. 15, No. 8, Apr. 15, 2005, pp. 2073-2077.
Williams et al. Foye's Principles of Medicinal Chemistry, 5th Edition, p. 50, 2002.
Wu et al., Brain Imaging of Nicotinic Receptor's in Alzheimer's Disease, Int J Alzheimer's Disease, vol. 2010, Article ID 548913, 11 pages.

ANTITUSSIVE COMPOSITIONS AND METHODS

CROSS-REFERENCE TO RELATED APPLICATIONS

This application claims the benefit of priority of U.S. provisional application Ser. No. 62/199,353, filed on Jul. 31, 2015, the contents of which is hereby incorporated by reference as if written herein in its entirety.

FIELD OF THE DISCLOSURE

The present disclosure relates to pharmaceutical compositions (i.e., antitussives) incorporating compounds capable of affecting nicotinic acetylcholinergic receptors (nAChRs), for example, as modulators of specific nicotinic receptor subtypes (specifically, the α7 nAChR subtype). The present disclosure also relates to methods for treating a wide variety of conditions and disorders, particularly those associated with suppressing cough.

BACKGROUND OF THE DISCLOSURE

Cough is the most common symptom for which patients seek medical advice from primary health care providers. Current antitussive therapies are minimally effective and have side effects that limit their utility. In the United States alone over 2 billion dollars are spent annually on over the counter cough remedies with questionable efficacy, potential toxicity, and abuse potential, with billions more spent annually in sick days and doctor's visits. Cough is the primary mechanism of transmission of airborne infections, including all forms of influenza, tuberculosis, and *Bordetella pertussis*, the gram negative bacterium causing whooping cough. As such, cough represents a major public health issue that is poorly treated with currently existing therapies. Currently existing cough medications include dextromethorphan and codeine; however these afford limited efficacy effects in clinical trials with significant side effects and are not suitable for chronic use. People suffering from coughing generally take throat lozenges, cough syrups, and cough drops, using these medications for symptomatic relief. While such medications presently exist, there is room for significant improvement in the efficacy of these treatments. Thus, there is a need for new antitussive compositions that are efficacious in suppressing cough.

SUMMARY OF THE DISCLOSURE

The present disclosure relates to pharmaceutical compositions (i.e., antitussives) incorporating compounds capable of affecting nicotinic acetylcholinergic receptors (nAChRs), for example, as modulators (e.g., agonist and/or partial agonist) of specific nicotinic receptor subtypes (specifically, the α7 nAChR subtype).

The compounds disclosed herein are of the azabicycloalkane category, and generally are azabicyclooctanes. The aryl group in the arylalkyl moiety is a 6-membered ring heteroaromatic, preferably 3-pyridinyl moieties, and the alkyl group is typically a $C_{1-4}$ alkyl. The substituent at the 3-position of the 1-azabicycloalkane is a carbonyl-containing functional group, preferably an amide, or similar functionality.

Accordingly, the inventors herein disclose methods that can provide relief or suppression of cough. Provided is an antitussive composition comprising a nicotinic receptor agonist (e.g., agonist and/or partial agonist) of specific nicotinic receptor subtypes (specifically, the α7 nAChR subtype). Provided is a method of suppressing cough in subjects in need thereof, comprising the step of administering to the subject a therapeutically effective amount of a composition comprising a nicotinic receptor agonist, specifically, the α7 nAChR subtype. Provided is an antitussive composition comprising a nicotinic receptor agonist, specifically, the α7 nAChR subtype, for use in human therapy. Provided is an antitussive composition comprising a nicotinic receptor agonist, specifically, the α7 nAChR subtype, for use in inducing suppression of cough. Provided is an antitussive composition comprising a nicotinic receptor agonist, specifically, the α7 nAChR subtype, for the manufacture of a medicament to treat cough.

BRIEF DESCRIPTION OF THE DRAWINGS

FIG. 4. Guinea pigs were pretreated intraperitoneally with drug vehicle (saline) or (2 S,3R)—N-(2-((3-pyridinyl)methyl)-1-azabicyclo[2.2.2]oct-3-yl)benzofuran-2-carboxamide (30 mg/kg). Respiration and cough reflexes were measured using a Buxco inhalation chamber connected to a Biopac data acquisition system. Thirty minutes after vehicle or drug administration, animals were challenged in sequence with ascending aerosol concentrations of citric acid (0.01M-0.3M), with each aerosol delivered for 5 minutes and with 5 minutes interval in between challenges. The cumulative coughs evoked were quantified and results are presented as a mean±standard error of the mean (SEM) of n experiments, where n refers to a single animal). The compound markedly inhibited citric acid evoked coughs. The compound markedly inhibited citric acid evoked coughing.

DETAILED DESCRIPTION OF THE DISCLOSURE

The compound described herein have the structure that is represented by Formula I:

Formula 1

For this compound, individual isomers thereof, mixtures thereof, including racemic mixtures, enantiomers, distereomers, and tautomers thereof, and the pharmaceutically acceptable salts thereof, are intended to be within the scope of the present disclosure.

Abbreviations and Definitions

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination. When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values that it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder or on the effecting of a clinical endpoint. The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partialagonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" is a substance that provides a level of stimulation to its binding partner that is intermediate between that of a full or complete antagonist and an agonist defined by any accepted standard for agonist activity. It will be recognized that stimulation, and hence, inhibition is defined intrinsically for any substance or category of substances to be defined as agonists, antagonists, or partial agonists.

As used herein, "intrinsic activity", or "efficacy," relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. See Hoyer, D. and Boddeke, H., *Trends Pharmacal Sci.* 14(7):270-5 (1993). Where such contextually specific evaluations are relevant, and how they might be relevant in the context of the present invention, will be apparent to one of ordinary skill in the art.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use.* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like. Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine. A salt of a compound can be made by reacting the appropriate compound in the form of the free base with the appropriate acid.

Nicotinic Receptor Agonists

Provided herein are antitussive compositions for suppressing cough comprising a nicotinic receptor agonist. Nicotinic receptor agonists are ligands that mimic the action of acetylcholine at nicotinic acetylcholine receptors. Provided herein is a list of nicotinic receptor agonists, specifically, the α7 nAChR subtype: A-582941, ABBF, ABT-418, ABT-594, acetylcholine, anabaseine, AR-R17779, AZD0328, choline, cytosine, DMBX-anabaseine, DMXB-A, epibatidine, GTS-21, imidacloprid, lobeline, JN403, MEM 3454, nicotine, PHA-543613, PNU-282987, pyridol, SEN12333, SSR18071, SSR180711, TC-5619, TC-6987, varenicline, 4BP-TQS, A 582941, A 844606, AR-R 17779 hydrochloride, 3-Bromocytisine, DMAB-anabaseine dihydrochloride, GTS 21 dihydrochloride, PHA-543613 hydrochloride, PHA 568487, PNU 282987, S 24795, SEN 12333, SSR 18071 hydrochloride, TC-1698 dihydrochloride, and pharmaceutically acceptable salts thereof. The nicotinic receptor agonists may be present in the form of their pharmaceutically acceptable salts, such as, but not limited to, an acid salt such as acetates, tartrates, chloride, phosphate, sulfates, sulfites, carbonates, bicarbonate and citrates.

An embodiment of the pharmaceutical compositions described herein is the (2R,3R; 2R,3S; 2S,3R; and 2S,3S)—N-(2-((3-pyridinyl)methyl)-1-azabicyclo[2.2.2]oct-3-yl) benzofuran-2-carboxamide and/or pharmaceutically acceptable salts thereof.

For this chiral compound, individual isomers thereof, mixtures thereof, including racemic mixtures, pure enantiomers, distereomers, and tautomers thereof, and the pharmaceutically acceptable salts thereof, are intended to be within the scope of the present disclosure.

Another embodiment as described herein, is the pure enantiomer, (2S,3R)—N-(2-((3-pyridinyl)methyl)-1-azabicyclo[2.2.2]oct-3-yl)benzofuran-2-carb oxamide and/or pharmaceutically acceptable salts thereof.

In yet another embodiment as described herein, the pharmaceutically acceptable salt of the pure enantiomer, (2S,3R)—N-(2-((3-pyridinyl)methyl)-1-azabicyclo[2.2.2]oct-3-yl)benzofuran-2-carboxamide is the hydrochloride salt.

Additional Antitussives

In certain embodiments, the antitussive composition comprises an additional antitussive chosen from ambroxol, apomorphine hydrochloride, beechwood creosote, benzonatate, camphor ethanedisulfonate, caramiphen edisylate, carbetapentane citrate, chlophendianol hydrochloride, codeine, codeine phosphate, codeine sulfate, dextromethorphan, dextromethorphan hydrobromide, diphenhydramine, diphenhydramine hydrochloride, fentanyl, fentanyl citrate, hydrocodone, hydromorphone hydrochloride, levorphanol tartrate, menthol, methadone hydrochloride, morphine, morphine sulfate, noscapine, noscapine hydrochloride, oxycodone hydrochloride, and oxymorphone hydrochloride, zinc gluconate. Expectorants In certain embodiments, the antitussive composition comprises an expectorant chosen from acetylcysteine, ammonium carbonate, ammonium chloride, antimony potassium tartrate, glycerin, guaifenesin, potassium iodide, sodium citrate, terpin hydrate, tolu balsam.

Mucolytics

In certain embodiments, the antitussive composition comprises a mucolytic chosen from acetylcysteine, ambroxol, bromhexine, carbocisteine, domiodol, dornase alfa, eprazinone, erdosteine, letosteine, mesna, neltenexine, sobrerol, stepronin, and tiopronin.

Nasal Decongestants

In certain embodiments, the antitussive composition comprises a nasal decongestant chosen from ephedrine, ephedrine hydrochloride, ephedrine sulfate, epinephrine bitartrate, hydroxyamphetamine hydrobromide, mephentermine sulfate, methoxamine hydrochloride, naphazoline hydrochloride, oxymetalozine hydrochloride, phenylpropanolamine hydrochloride, propylhexedrine, psuedoephedrine hydrochloride, tetrahydrozoline hydrochloride, and xylometazoline hydrochloride. Antihistamines in certain embodiments, the antitussive composition comprises an antihistamine chosen from antazoline, azatadine, brompheniramine, brompheniramine mepyramine, carbinoxamine, chlorcyclizine, chlorpheniramine, chlorpheniramine, clemastine, cyclizine, cyproheptadine, dexchlorpheniramine, dimenhydrinate, dimetindene, diphenhydramine, diphenhydramine, doxylamine, doxylamine, hydroxyzine, ketotifen, meclizine, pheniramine, promethazine, trimeprazine, and triprolidine.

Opioid Analgesics

In certain embodiments, the antitussive composition comprises an opioid analgesic chosen from codeine, diphenoxylate, fentanyl, hydrocodone, hydromorphone, levorphanol, meperidine, methadone, morphine, oxycodone, oxymorphone, and propoxyphene.

Non-opioid Analgesics In certain embodiments, the antitussive composition comprises a non-opioid analgesic is chosen from acetaminophen, aspirin, ibuprofen and naproxen.

I. Pharmaceutical Compositions

The compounds described herein can be incorporated into pharmaceutical compositions and used to prevent a condition or disorder in a subject susceptible to such a condition or disorder, and/or to treat a subject suffering from the condition or disorder.

In one embodiment, such condition or disorder is suppressing cough.

The pharmaceutical compositions described herein include nicotinic receptor agonists, specifically of the α7 nAChR subtype.

An embodiment of the pharmaceutical compositions described herein is the (2R,3R; 2R,3S; 2S,3R; and 2S,3S)—N-(2-((3-pyridinyl)methyl)-1-azabicyclo[2.2.2]oct-3-yl)benzofuran-2-carboxamide and/or pharmaceutically acceptable salts thereof.

For this chiral compound, individual isomers thereof, mixtures thereof, including racemic mixtures, pure enantiomers, distereomers, and tautomers thereof, and the pharmaceutically acceptable salts thereof, are intended to be within the scope of the present disclosure.

Another embodiment as described herein, is the pure enantiomer, (2S,3R)—N-(2-((3-pyridinyl)methyl)-1-azabicyclo[2.2.2]oct-3-yl)benzofuran-2-carboxamide and/or pharmaceutically acceptable salts thereof.

In yet another embodiment, the pharmaceutically acceptable salt of the pure enantiomer, (2S,3R)—N-(2-((3-pyridinyl)methyl)-1-azabicyclo[2.2.2]oct-3-yl)benzofuran-2-carboxamide is the hydrochloride salt.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions can be formulated in unit dose form, or in multiple or subunit doses. Preferred compositions are in liquid or semisolid form. Compositions including a liquid pharmaceutically inert carrier such as water or other pharmaceutically compatible liquids or semisolids can be used. The use of such liquids and semisolids is well known to those of skill in the art. The compositions can also be administered via injection, i.e., intravenously, intramuscularly, subcutaneously, intraperitoneally, intraarterially, intrathecally; and intracerebroventricularly. Intravenous administration is the preferred method of injection. Suitable carriers for injection are well known to those of skill in the art and include 5% dextrose solutions, saline, and phosphate-buffered saline. The compounds can also be administered as an infusion or injection (e.g., as a suspension or as an emulsion in a pharmaceutically acceptable liquid or mixture of liquids).

The formulations can also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations can depend on the particular composition used and the particular subject receiving the treatment. These formulations can contain a liquid carrier that can be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, upon administration, the active ingredients interact with receptor sites within the body of the subject that affect suppressing cough. More specifically, in suppressing cough, preferable administration is designed to optimize the effect upon those relevant nicotinic acetylcholine receptor (nAChR) subtypes, e.g., specifically of the α7 nAChR subtype, that have an effect upon suppressing cough, while minimizing the effects upon muscle-type receptor subtypes. Other suitable methods for administering the compounds of the present disclosure are described in U.S. Pat. No. 5,604,231 to Smith et al., the contents of which are hereby incorporated by reference.

In certain circumstances, the compounds described herein can be employed as part of a pharmaceutical composition with other compounds intended to prevent or treat a particular disorder. In addition to effective amounts of the compounds described herein, the pharmaceutical compositions can also include various other components as additives or adjuncts. Exemplary pharmaceutically acceptable components or adjuncts which are employed in relevant circumstances include antioxidants, free-radical scavenging agents, peptides, growth factors, antibiotics, bacteriostatic agents, immunosuppressives, anticoagulants, buffering agents, anti-inflammatory agents, anti-pyretics, time-release binders, anesthetics, steroids, vitamins, minerals and corticosteroids. Such components can provide additional therapeutic benefit, act to affect the therapeutic action of the pharmaceutical composition, or act towards preventing any potential side effects that can be imposed as a result of administration of the pharmaceutical composition.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. When treating a cough, an effective amount of compound is an amount sufficient to pass across the blood-brain barrier of the subject, to bind to relevant receptor sites in the brain of the subject and to modulate the activity of relevant nAChR subtypes (e.g., specifically of the α7 nAChR subtype, that have an effect upon suppressing cough). Prevention of the disorder is manifested by delaying the onset of the symptoms of the disorder. Treatment of the disorder is manifested by a decrease in the symptoms associated with the disorder or an amelioration of the recurrence of the symptoms of the disorder. Preferably, the effective amount is sufficient to obtain the desired result, but insufficient to cause appreciable side effects.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to modulate the activity of relevant nAChRs subtypes (e.g., specifically of the α7 nAChR subtype, that have an effect upon suppressing cough), but the amount should be insufficient to induce effects on skeletal muscles and ganglia to any significant degree. The effective dose of compounds will of course differ from patient to patient, but in general includes amounts starting where desired therapeutic effects occur but below the amount where muscular effects are observed.

The compounds, when employed in effective amounts in accordance with the method described herein, are selective to certain relevant nAChRs subtypes (e.g., specifically of the α7 nAChR subtype, that have an effect upon suppressing cough), but do not significantly activate receptors associated with undesirable side effects at concentrations at least greater than those required for eliciting the release of dopamine or other neurotransmitters. By this is meant that a particular dose of compound effective in preventing and/or treating a cough is essentially ineffective in eliciting activation of certain ganglionic-type nAChRs at concentration higher than 5 times (5×), preferably higher than 100 times (100×), and more preferably higher than 1,000 times (1000×) than those required for modulation of neurotransmitter release.

The compounds described herein, when employed in effective amounts in accordance with the methods described herein, can provide some degree of preventing and/or suppressing cough, the progression of cough, ameliorate symptoms of cough, and ameliorate to some degree of the recurrence of cough. The effective amounts of those compounds are typically below the threshold concentration required to elicit any appreciable side effects, for example those effects relating to skeletal muscle. The compounds can be administered in a therapeutic window in which certain cough disorders are treated and certain side effects are avoided. Ideally, the effective dose of the compounds described herein is sufficient to provide the desired effects upon the cough but is insufficient (i.e., is not at a high enough level) to provide undesirable side effects. Preferably, the compounds are administered at a dosage effective for treating a cough disorder but less than ⅕, and often less than 1/10, the amount required to elicit certain side effects to any significant degree.

Compounds may be administered orally at a dose of from 0.1 mg to 1 g/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

II. Methods of Using the Compounds and/or Pharmaceutical Compositions

Provided is a method of suppressing cough in a subject comprising administering to the subject in need thereof a therapeutically effective amount of (2S,3R)—N-(2-((3-pyridinyl)methyl)-1-azabicyclo[2.2.2]oct-3-yl)benzofuran-2-carboxamide or a pharmaceutically acceptable salt thereof.

In another embodiment, wherein the pharmaceutically acceptable salt of (2S,3R)—N-(2-((3-pyridinyl)methyl)-1-azabicyclo[2.2.2]oct-3-yl)benzofuran-2-carboxamide is the hydrochloride salt.

In another embodiment, wherein the method comprises administering to said subject one or more additional pharmaceutically active ingredients chosen from antitussives other than nicotine or a derivatives thereof, antihistamines, antipyretics, expectorants, mucolytics, nasal decongestants, non-opiate analgesics oropioid analgesics.

In another embodiment, wherein the antitussive is chosen from ambroxol, apomorphine hydrochloride, beechwood creosote, benzonatate, camphor ethanedisulfonate, caramiphen edisylate, carbetapentane citrate, chlophendianol hydrochloride, codeine, codeine phosphate, codeine sulfate, dextromethorphan, dextromethorphan hydrobromide, diphenhydramine, diphenhydramine hydrochloride, fentanyl, fentanyl citrate, hydrocodone, hydromorphone hydrochloride, levorphanol tartrate, menthol, methadone hydrochloride, morphine, morphine sulfate, noscapine, noscapine hydrochloride, oxycodone hydrochloride or oxymorphone hydrochloride.

In another embodiment, wherein the expectorant is chosen from acetylcysteine, ammonium carbonate, ammonium chloride, antimony potassium tartrate, glycerin, guaifenesin, potassium iodide, sodium citrate, terpin hydrate, tolu balsam.

In another embodiment, wherein the mucolytic is chosen from acetylcysteine, ambroxol, bromhexine, carbocisteine, domiodol, dornase alfa, eprazinone, erdosteine, letosteine, mesna, neltenexine, sobrerol, stepronin or tiopronin.

In another embodiment, wherein the nasal decongestant is chosen from ephedrine, ephedrine hydrochloride, ephedrine sulfate, epinephrine bitartrate, hydroxyamphetamine hydrobromide, mephentermine sulfate, methoxamine hydrochloride, naphazoline hydrochloride, oxymetalozine hydrochloride, phenylpropanolamine hydrochloride, propylhexedrine, psuedoephedrine hydrochloride, tetrahydrozoline hydrochloride, or xylometazoline hydrochloride.

In another embodiment, wherein the antihistamine is chosen from antazoline, azatadine, brompheniramine, brompheniramine mepyramine, carbinoxamine, chlorcyclizine, chlorpheniramine, chlorpheniramine, clemastine, cyclizine, cyproheptadine, dexchlorpheniramine, dimenhydrinate, dimetindene, diphenhydramine, diphenhydramine, doxylamine, doxylamine, hydroxyzine, ketotifen, meclizine, pheniramine, promethazine, trimeprazine or triprolidine.

In another embodiment, wherein the opioid analgesic is chosen from codeine, diphenoxylate, fentanyl, hydrocodone, hydromorphone, levorphanol, meperidine, methadone, morphine, oxycodone, oxymorphone or propoxyphene.

In another embodiment, the non-opioid analgesic is chosen from acetaminophen, aspirin, ibuprofen or naproxen.

In yet another embodiment, wherein (2S,3R)—N-(2-((3-pyridinyl)methyl)-1-azabicyclo[2.2.2]oct-3-yl)benzofuran-2-carboxamide is administered in the form of a capsule, elixir, fast-melt strip, gum, lozenge, liquid, lotion, nasal-inhaled spray, oral-inhaled spray, orally disintegrating tablet, syrup, tablet, or transdermal patch.

In another embodiment, the subject is a human.

In yet another embodiment, wherein (2S,3R)—N-(2-((3-pyridinyl)methyl)-1-azabicyclo[2.2.2]oct-3-yl)benzofuran-2-carboxamide is administered once a day.

In yet another embodiment, wherein (2S,3R)—N-(2-((3-pyridinyl)methyl)-1-azabicyclo[2.2.2]oct-3-yl)benzofuran-2-carboxamide is administered twice a day.

In yet another embodiment, wherein (2S,3R)—N-(2-((3-pyridinyl)methyl)-1-azabicyclo[2.2.2]oct-3-yl)benzofuran-2-carboxamide is administered at least three times a day.

In another embodiment, the cough is a symptom of one or more conditions chosen from sneezing, rhinorrhea, nasal obstruction, nasal congestion, nasal pruritus, rhinorrhea, allergies, allergic vasomotor rhinitis (hay fever), seasonal allergic vasomotor rhinitis, perennial allergic vasomotor rhinitis, a respiratory disease, a cold, acute bronchitis, chronic bronchitis, asthmatic bronchitis, bronchiectasis, pneumonia, lung tuberculosis, silicosis, silicotuberculosis, pulmonary cancer, upper respiratory inflammation, pharyngitis, laryngitis, nasal catarrh, asthma, bronchial asthma, infantile asthma, pulmonary emphysema, pneumoconiosis, pulmonary fibrosis, pulmonary silicosis, pulmonary suppuration, pleuritis, tonsillitis, cough hives, post-viral cough, gastreoesophageal reflux disease, post-nasal drip, nasal congestion, sinusitis, whooping cough or the cough results from a procedure chosen from a bronchography or a bronchoscopy.

In an embodiment, wherein the cough is acute.

In an embodiment, wherein the cough is subacute.

In an embodiment, wherein the cough is chronic.

In an embodiment, wherein (2S,3R)—N-(2-((3-pyridinyl)methyl)-1-azabicyclo[2.2.2]oct-3-yl)benzofuran-2-carboxamide is administered orally or by intramuscular injection, subcutaneous injection, intraperitoneal injection, intrathecal, sublingualmal.

In an embodiment, wherein the method of suppressing or reducing cough by orally consuming a cough suppressing or reducing amount of (2S,3R)—N-(2-((3-pyridinyl)methyl)-1-azabicyclo[2.2.2]oct-3-yl)benzofuran-2-carboxamide or a pharmaceutically acceptable salt thereof.

EXAMPLES

Example 1

Cough Reflex Sensitivity Study

Capsaicin, the pungent extract of red peppers, has been shown in over three decades of clinical experience to experimentally induce cough in a safe, dose-dependent and reproducible manner. Thus, capsaicin cough challenge testing has become an important tool in clinical research, allowing for the accurate measurement of the effect of a pharmacological or other intervention on the sensitivity of the cough reflex. The standard endpoint measured in capsaicin cough challenge testing is the concentration of capsaicin inducing 5 or more coughs ($C_5$). In healthy volunteers, this endpoint has been demonstrated to be highly reproducible, in the short-term (20 minutes to 14 days) and long term (months to years). Standard capsaicin challenge methodology was used in this study to assess the effect of e-cig vapor exposure on cough reflex sensitivity. Electronic cigarettes are electronic nicotine delivery devices. A cartridge within the e-cig contains nicotine in a vehicle of distilled water, as well as either vegetable glycerin or propylene glycol. A lithium battery within the e-cig generates heat, thus vaporizing the nicotine solution. No combustion is involved in the creation of the nicotine-containing vapor that is inhaled by the user and promptly absorbed from the respiratory tract into the bloodstream.

Capsaicin Cough Challenge

Subjects inhaled single, vital-capacity breaths of ascending, doubling concentrations (range 0.49 µM to 1,000 µM) of aerosolized capsaicin solution, administered via a compressed air-driven nebulizer controlled by a dosimeter, with 1-minute intervals between inhalations, until 5 or more coughs resulted in the 15 seconds following an inhalation. Placebo saline breaths were randomly interspersed between capsaicin doses to increase challenge blindness. The end point of capsaicin challenge testing is the concentration of capsaicin inducing 5 or more coughs (C5).

Subjects

Thirty adult lifetime nonsmokers were enrolled after providing written, informed consent for this study, which was approved by the Institutional Review Board of the Albert Einstein College of Medicine, Bronx, N.Y. (IRB#2014-3288). Subjects were without history of asthma, gastroesophageal reflux disease, or symptoms suggestive of acute viral upper respiratory tract infection (common cold) or allergies within 4 weeks of enrollment. Subjects were not receiving medication known to affect cough reflex sensitivity.

Study Design

Upon enrollment, subjects underwent capsaicin challenge testing on Day 1 to establish their baseline cough reflex sensitivity. On study Day 2 subjects underwent an electronic cigarette vaping session. While in a relaxed, seated position, subjects inhaled a total of 30 puffs (one puff every 30 seconds) from a disposable electronic cigarette (Blu, Classic Tobacco flavor, Lorillard Technologies, Greensboro, N.C., USA). A disposable Blu electronic cigarette contains 20-24 mg of nicotine, and delivers approximately 400 puffs of nicotine-containing vapor. The ingredients of the vapor include distilled water, nicotine, vegetable glycerin, natural flavors, artificial flavors and citric acid (from Blu website, accessed Jan. 2, 2015). Thus, 30 puffs of the e-cigarette delivered approximately 1.5-1.8 mg of nicotine. In comparison, the estimated nicotine intake from a tobacco cigarette is in the range of 1.07-2.6 mg, depending on the brand. Fifteen minutes after the conclusion of the e-cigarette session, subjects underwent capsaicin cough challenge. On study Day 3, approximately 24 hours after the vaping session, subjects underwent repeat capsaicin challenge. In addition, the number of coughs induced by each of the 30 puffs of the e-cig was tabulated. A cough number of 5 was assigned for ≥5 coughs. A subgroup of 8 subjects who demonstrated large degrees of cough reflex sensitivity inhibition after e-cig exposure, (defined as ≥2 doubling-concentration increase in $C_5$), underwent a repeat protocol identical to the above but with a disposable non-nicotine containing e-cigarette with similar vehicle (BlueStar, Full Tobacco Flavor, Las Vegas, Nev., USA). Subjects were unaware that the e-cig used in this portion of the study was nicotine free. Cough reflex sensitivity ($C_5$) was analyzed employing mixed-effects modeling, with subsequent post-hoc analysis correcting for multiple comparisons using the Tukey-Kramer approach. Pre and post e-cig exposure differences in $C_5$ response and number of coughs between nicotine and non-nicotine containing e-cigs were compared using Wilcoxon's signed-rank test. Statistical analyses were performed using SAS version 9.3 software (Cary, N.C., USA).

Results

Figure 1:
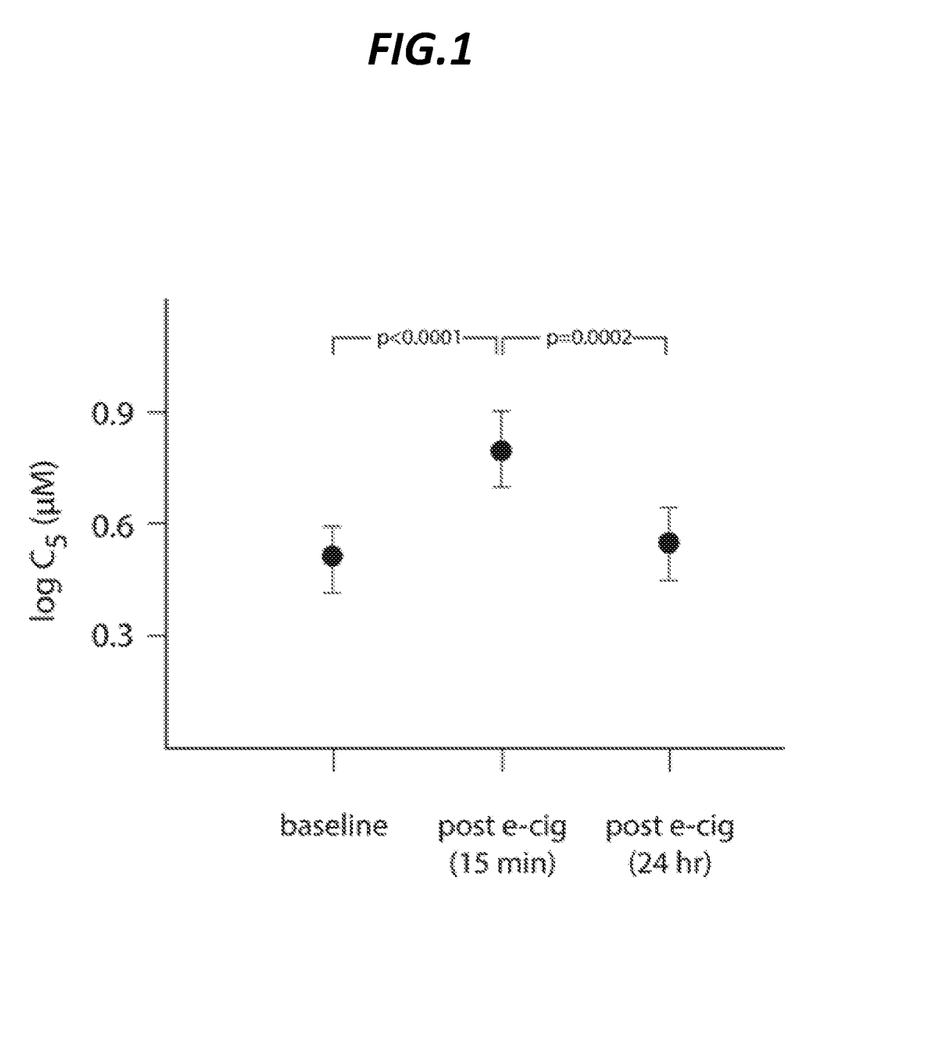
FIG. 1. Shows the change in cough reflex sensitivity ($C_5$) from baseline after electronic cigarette exposure (30 puffs delivered 30 seconds apart) in 30 healthy adult nonsmokers. Significant inhibition of cough reflex sensitivity (increase in $C_5$) occurred 15 minutes after exposure (p<0.0001). This effect was transient, as $C_5$ returned to baseline 24 hours after exposure (p=0.0002 vs. post-15-minute value). $C_5$=concentration of capsaicin inducing ≥5 coughs.
Figure 2:
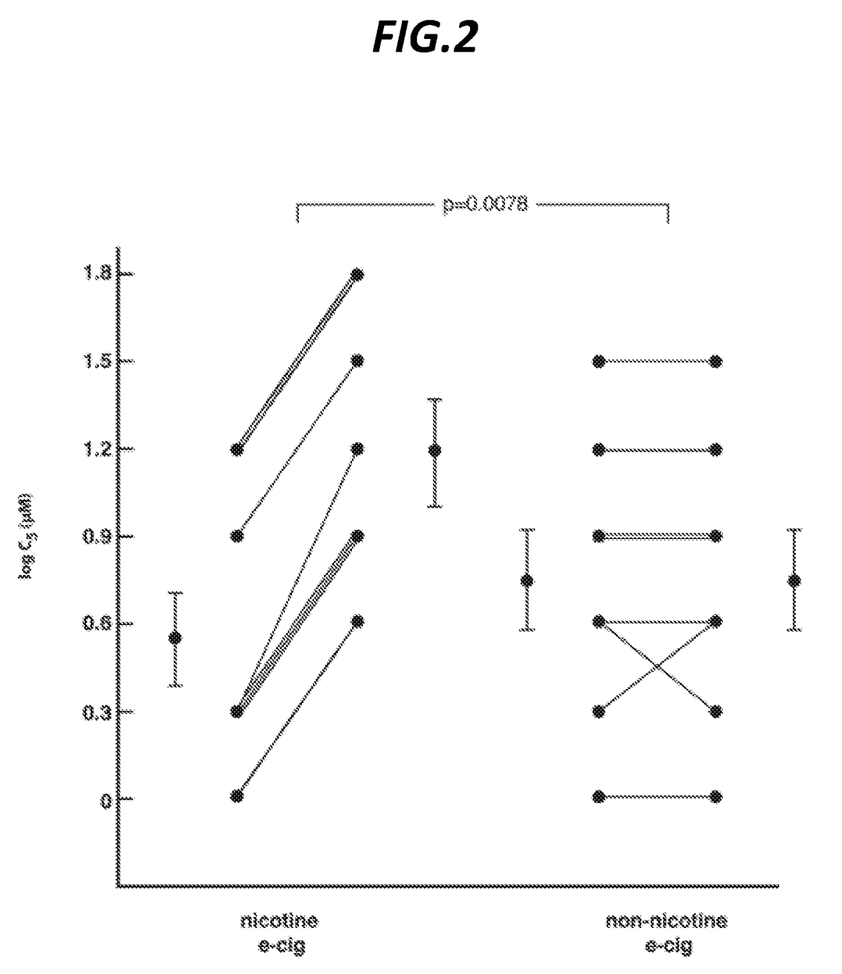
FIG. 2. Shows a comparison of the effect of nicotine-containing and non-nicotine-containing electronic cigarette exposure on cough reflex sensitivity ($C_5$) in a subgroup of 8 subjects who had demonstrated the largest increments in $C_5$ (greatest degree of inhibition of cough reflex sensitivity) after nicotine-containing electronic cigarette use. The non-nicotine-containing electronic cigarette exposure did not affect cough reflex sensitivity as did the nicotine-containing product (p=0.0078 for difference in change in $C_5$). $C_5$=concentration of capsaicin inducing ≥5 coughs.

Thirty subjects (15 female; age 29.8±4.5) were enrolled and completed the study. After electronic cigarette exposure, cough reflex sensitivity was significantly diminished (i.e., $C_5$ was significantly increased) compared to baseline. This effect was transient, as demonstrated by the enhancement of cough reflex sensitivity back to baseline levels 24 hours after the e-cig exposure. Mean log $C_5$ at baseline was 0.50±0.09 (SEM); 15 minutes after electronic cigarette exposure 0.79±0.11; and 24 hours subsequently 0.55±0.10. Employing mixed-effects modeling, with subsequent post-hoc analysis correcting for multiple comparisons using the Tukey-Kramer approach, the difference between log $C_5$ at baseline and post e-cig exposure was significant (difference in mean log $C_5$ −0.29, 95% CI−0.43 to −0.15, p<0.0001) as was the difference between post e-cig use and 24 hours later (difference in mean log $C_5$ 0.24, 95% CI 0.10-0.38, p=0.0002) (FIG. 1). In terms of individual responses, 23 of 30 subjects demonstrated an inhibition of cough reflex sensitivity (increased $C_5$) after e-cig exposure; 5 subjects had no change; and 2 subjects had a one-doubling concentration decrease in $C_5$. Twenty six of the 30 subjects coughed to some degree in response to inhalation of the 30 puffs of the e-cig. The median number of coughs for the study group was 15.5 with a range of 0-114 coughs. There was no correlation between the number of coughs induced by e-cig inhalation and subsequent change in cough reflex sensitivity ($C_5$), as demonstrated by computation of the Spearman correlation coefficient, with Fisher's z-transformation. The point estimate of this correlation was −0.20 with 95% CI (−0.62, 0.23) and was not significantly different from zero (p=0.453). To further investigate the role of nicotine in our observations, we performed an additional exploratory analysis by repeating an identical protocol of cough reflex sensitivity measurement before and after exposure to a non-nicotine-containing disposable electronic cigarette in a subgroup of subjects. All 8 subjects who had demonstrated large degrees of inhibition of cough reflex sensitivity after exposure to the nicotine-containing e-cig, defined as a≥2 doubling-concentration increase in $C_5$, agreed to participate in a follow-up study of a different brand of e-cigarette. Subjects were not aware that the e-cig being evaluated in the second phase of the study did not contain nicotine. No inhibition of cough reflex sensitivity was observed after exposure to the non-nicotine-containing e-cig, in contrast to the change in $C_5$ after use of the nicotine-containing e-cig (median difference in $\Delta C_5$ 0.6, range 0.6-0.9, p=0.0078, Wilcoxon's signed-ranks test) (FIG. 2). In addition, significantly less coughing was observed after 30 puffs of the non-nicotine-containing e-cig compared with the nicotine-containing product; median difference in Δ number of coughs 6, range 0-21, p=0.0156. The results indicate that a single exposure to electronic cigarette vapor, approximating the nicotine delivery of one tobacco cigarette, significantly inhibits cough reflex sensitivity in a group of healthy adult nonsmokers as measured by capsaicin inhalation cough challenge testing. The effect is transient, as cough reflex sensitivity returned to baseline 24 hours after e-cig use. These findings are consistent with observations in healthy smokers of tobacco cigarettes, whose cough reflex sensitivity is suppressed relative to nonsmokers. The demonstration that cough reflex sensitivity is significantly enhanced as soon as two weeks after smoking cessation supports the hypothesis that inhibition of cough reflex sensitivity is due to desensitization of cough receptors within the airway epithelium caused by chronic exposure to tobacco smoke. Furthermore, as this effect is promptly reversible even after years of tobacco smoking, cough reflex sensitivity is apparently a dynamic phenomenon, able to be modulated by the presence or absence of stimuli such as tobacco smoke. Given that these previous studies were performed in chronic tobacco cigarette smokers, the observations of the present study are perhaps more remarkable in that significant inhibition of cough reflex sensitivity was demonstrated after a single brief exposure to an electronic cigarette. In an attempt to gain insight as to the causative agent within the electronic cigarette vapor that led to significant inhibition of cough reflex sensitivity, we performed an exploratory analysis of a subgroup of our 30 subjects. Eight of the 30 subjects with the greatest degree of cough reflex suppression (defined as an elevation of capsaicin $C_5$≥2 doubling concentrations) after nicotine-containing e-cig exposure were subsequently exposed in a similar manner to a non-nicotine-containing e-cig with similar flavoring and vehicle. The absence of an effect on cough reflex sensitivity implicates nicotine as the agent within the e-cig vapor causing the inhibition of cough reflex sensitivity that we observed. Nicotine has been demonstrated in animals and man to have a peripheral, rapid-onset, cough-inducing effect, probably through stimulation of nicotinic acetylcholine receptors (nAChRs) expressed on sensory terminals of cough receptors within the airway mucosa. These observations may be relevant to the findings of the present study, since most of our subjects did cough immediately and transiently in response to e-cig inhalation, yet demonstrated inhibition of cough reflex sensitivity when measured 15 minutes after completion of the e-cig vaping session. In the subgroup of subjects who also underwent an exposure to a non-nicotine-containing electronic cigarette, less cough occurred during the vaping session, and inhibition of cough reflex sensitivity was absent. Thus, the results of our study may be an illustration of a dual action of nicotine: an acute, peripheral tussive effect, and a delayed, central antitussive effect. The putative action of nicotine as a centrally acting inhibitor of cough reflex sensitivity introduces the concept of nicotinic receptor agonists as potential therapeutic antitussive agents.

Example 2

Figure 3:
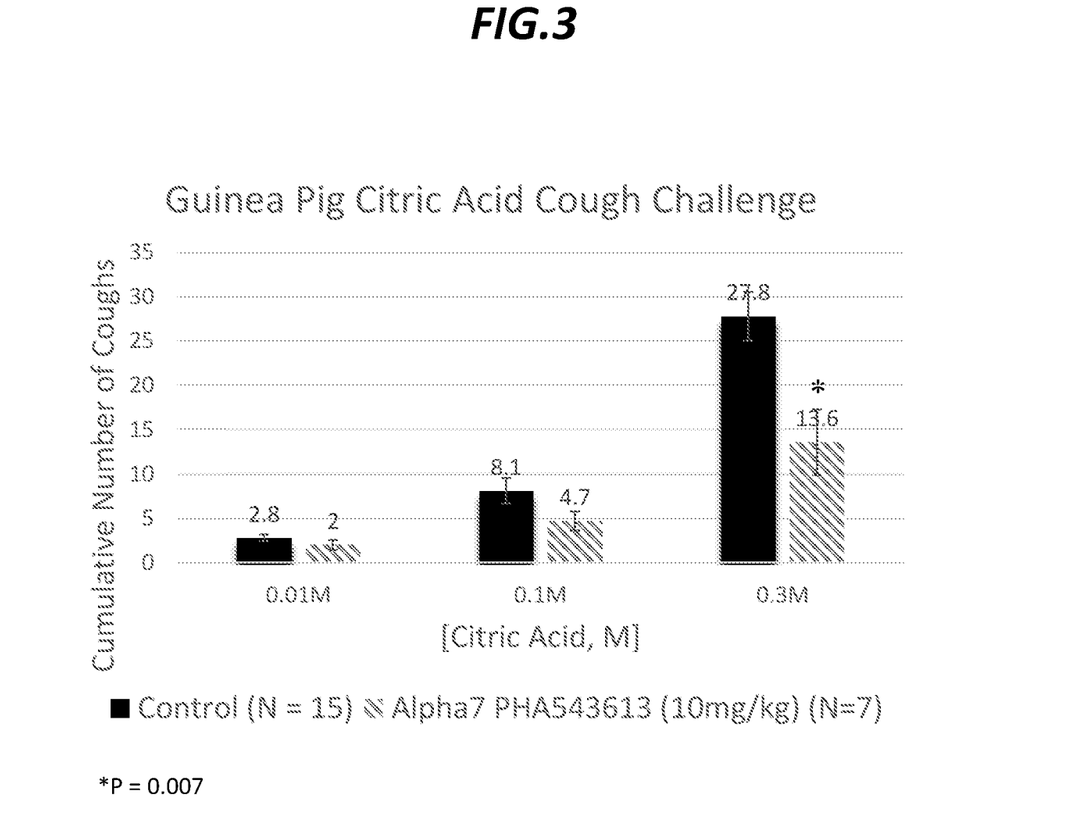
FIG. 3. Guinea pigs were pretreated intraperitoneally with drug vehicle (saline), α7 PHA543613 (10 mg/kg). Respiration and cough reflexes were measured using a Buxco inhalation chamber connected to a Biopac data acquisition system. Thirty minutes after vehicle or drug administration, animals were challenged in sequence with ascending aerosol concentrations of citric acid (0.01M-0.3M), with each aerosol delivered for 5 minutes and with 5 minutes interval in between challenges. The cumulative coughs evoked were quantified and results are presented as a mean±standard error of the mean (SEM) of n experiments, where n refers to a single animal). The compound markedly inhibited citric acid evoked coughs.
Figure 4:
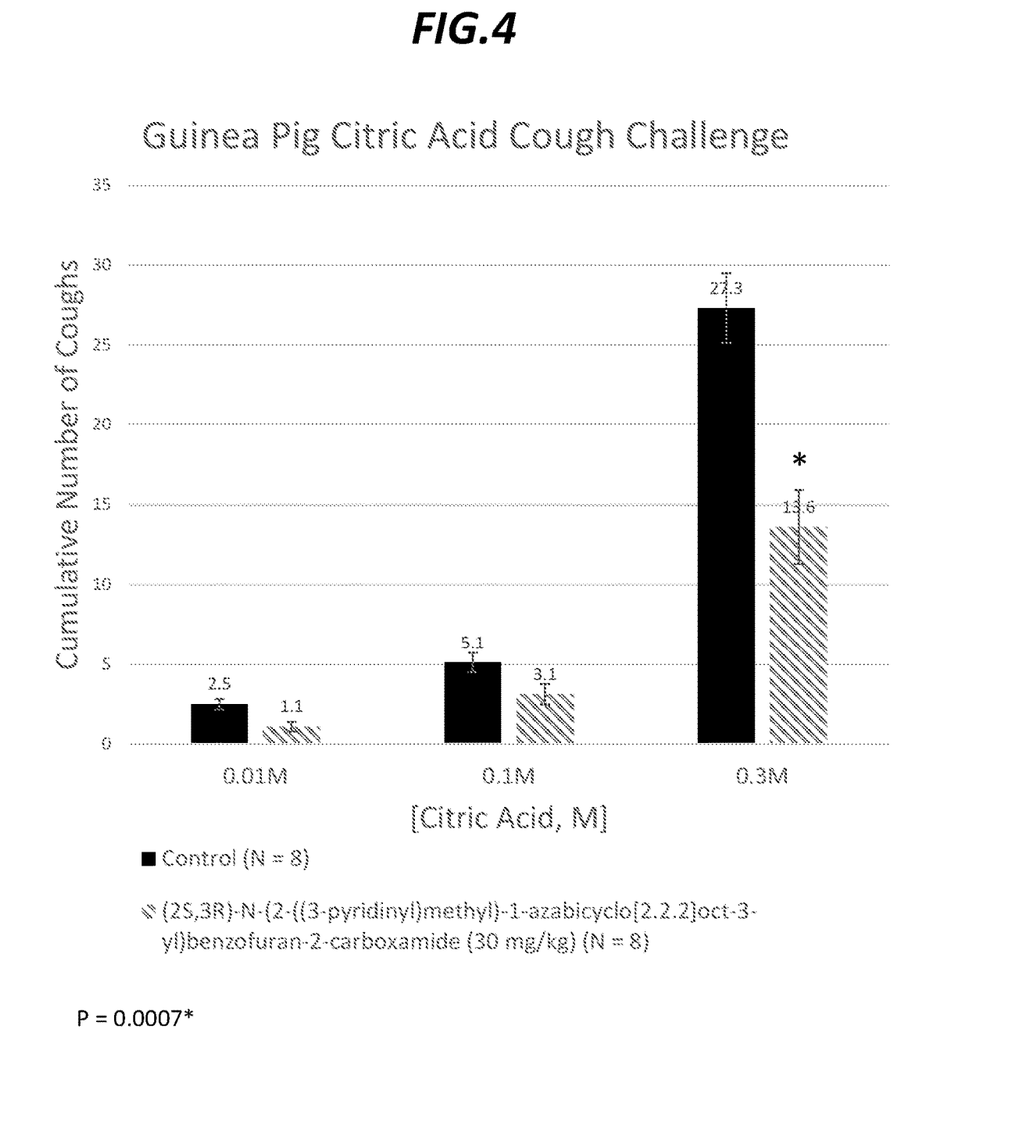

(2S,3R)—N-(2-(3-pyridinyl)methyl)-1-azabicyclo [2.2.2]oct-3-yl)benzofuran-2-carboxamide Inhibits Citric Acid Evoked Coughing in Guinea Pigs Cough suppression was evaluated in conscious guinea pigs using a citric acid inhalation model (Smith et al., 2012). Guinea pigs were pretreated intraperitoneally with drug vehicle (saline), α7 PHA543613 (10 mg/kg) (FIG. 3), or (2S,3R)—N-(2-(3-pyridinyl)methyl)-1-azabicyclo[2.2.2]oct-3-yl)benzofuran-2-carboxamide (30 mg/kg) (FIG. 4). Respiration and cough reflexes were measured using a Buxco inhalation chamber connected to a Biopac data acquisition system. Thirty minutes after vehicle or drug administration, animals were challenged in sequence with ascending aerosol concentrations of citric acid (0.01M-0.3M), with each aerosol delivered for 5 minutes and with 5 minutes interval in between challenges. The cumulative coughs evoked were quantified and results are presented as a mean±standard error of the mean (SEM) of n experiments, where n refers to a single animal). Studies were performed using a nonpaired parallel group design. Differences amongst group means were evaluated by t-test or ANOVA, with a p<0.05 considered statistically significant which is represented by an asterisk (*) in FIG. 3 and FIG. 4.

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A method of suppressing cough in a subject comprising administering to the subject in need thereof a therapeutically effective amount of (2S,3R)—N-(2-((3-pyridinyl)methyl)-1-azabicyclo[2.2.2]oct-3-yl)benzofuran-2-carboxamide or a pharmaceutically acceptable salt thereof.

2. The method of claim 1 wherein the pharmaceutically acceptable salt is the hydrochloride salt.

3. The method of claim 1 further comprising administering to said subject one or more additional pharmaceutically active ingredients chosen from antitussives other than nicotine or a derivative thereof, antipyretics, expectorants, mucolytics, nasal decongestants, antihistamines, opioid analgesics, or non-opiate analgesics.

4. The method of claim 3 wherein the antitussive is chosen from ambroxol, apomorphine hydrochloride, beechwood creosote, benzonatate, camphor ethanedisulfonate, caramiphen edisylate, carbetapentane citrate, chlophendianol hydrochloride, codeine, codeine phosphate, codeine sulfate, dextromethorphan, dextromethorphan hydrobromide, diphenhydramine, diphenhydramine hydrochloride, fentanyl, fentanyl citrate, hydrocodone, hydromorphone hydrochloride, levorphanol tartrate, menthol, methadone hydrochloride, morphine, morphine sulfate, noscapine, noscapine hydrochloride, oxycodone hydrochloride, oxymorphone hydrochloride or zinc gluconate.

5. The method of claim 3 wherein the expectorant is chosen from acetylcysteine, ammonium carbonate, ammonium chloride, antimony potassium tartrate, glycerin, guaifenesin, potassium iodide, sodium citrate, terpin hydrate, or tolu balsam.

6. The method of claim 3 wherein the mucolytic is chosen from acetylcysteine, ambroxol, bromhexine, carbocisteine, domiodol, dornase alfa, eprazinone, erdosteine, letosteine, mesna, neltenexine, sobrerol, stepronin, or tiopronin.

7. The method of claim 3 wherein the nasal decongestant is chosen from ephedrine, ephedrine hydrochloride, ephedrine sulfate, epinephrine bitartrate, hydroxyamphetamine hydrobromide, mephentermine sulfate, methoxamine hydrochloride, naphazoline hydrochloride, oxymetalozine hydrochloride, phenylpropanolamine hydrochloride, propylhexedrine, psuedoephedrine hydrochloride, tetrahydrozoline hydrochloride, or xylometazoline hydrochloride.

8. The method of claim 3 wherein the antihistamine is chosen from antazoline, azatadine, brompheniramine, brompheniramine mepyramine, carbinoxamine, chlorcyclizine, chlorpheniramine, chlorpheniramine, clemastine, cyclizine, cyproheptadine, dexchlorpheniramine, dimenhydrinate, dimetindene, diphenhydramine, diphenhydramine, doxylamine, doxylamine, hydroxyzine, ketotifen, meclizine, pheniramine, promethazine, trimeprazine, or triprolidine.

9. The method of claim 3 wherein the opioid analgesic is chosen from codeine, diphenoxylate, fentanyl, hydrocodone, hydromorphone, levorphanol, meperidine, methadone, morphine, oxycodone, oxymorphone, or propoxyphene.

10. The method of claim 3 wherein the non-opioid analgesic is chosen from acetaminophen, aspirin, ibuprofen, or naproxen.

11. The method of claim 3 wherein (2S,3R)—N-(2-((3-pyridinyl)methyl)-1-azabicyclo[2.2.2]oct-3-yl)benzofuran-2-carboxamide is administered in the form of a capsule, elixir, fast-melt strip, gum, lozenge, liquid, lotion, nasal-inhaled spray, oral-inhaled spray, orally disintegrating tablet, syrup, tablet, or transdermal patch.

12. The method as recited in claim 1 wherein the subject is a human.

13. The method of claim 1 wherein (2S,3R)—N-(2-((3-pyridinyl)methyl)-1-azabicyclo[2.2.2]oct-3-yl)benzofuran-2-carboxamide is administered once a day.

14. The method of claim 1 wherein (2S,3R)—N-(2-((3-pyridinyl)methyl)-1-azabicyclo[2.2.2]oct-3-yl)benzofuran-2-carboxamide is administered twice a day.

15. The method of claim 1 wherein (2S,3R)—N-(2-((3-pyridinyl)methyl)-1-azabicyclo[2.2.2]oct-3-yl)benzofuran-2-carboxamide is administered at least three times a day.

16. The method of claim 1 wherein the cough is a symptom of one or more conditions chosen from sneezing, rhinorrhea, nasal obstruction, nasal congestion, nasal pruritus, rhinorrhea, allergies, allergic vasomotor rhinitis (hay fever), seasonal allergic vasomotor rhinitis, perennial allergic vasomotor rhinitis, a respiratory disease, a cold, acute bronchitis, chronic bronchitis, asthmatic bronchitis, bronchiectasis, pneumonia, lung tuberculosis, silicosis, silicotuberculosis, pulmonary cancer, upper respiratory inflammation, pharyngitis, laryngitis, nasal catarrh, asthma, bronchial asthma, infantile asthma, pulmonary emphysema, pneumoconiosis, pulmonary fibrosis, pulmonary silicosis, pulmonary suppuration, pleuritis, tonsillitis, cough hives, postviral cough, gastreoesophageal reflux disease, post-nasal drip, nasal congestion, sinusitis, whooping cough or the cough results from a procedure chosen from a bronchography or a bronchoscopy.

17. The method of claim 1 wherein the cough is acute.

18. The method of claim 1 wherein the cough is chronic.

19. The method of claim 1 wherein (2S,3R)—N-(2-((3-pyridinyl)methyl)-1-azabicyclo[2.2.2]oct-3-yl)benzofuran-2-carboxamide is administered orally or by intramuscular injection, subcutaneous injection, intraperitoneal injection, intrathecal, sublingualmal.

20. A method of suppressing or reducing cough by orally consuming a cough suppressing or reducing amount of (2S,3R)—N-(2-((3-pyridinyl)methyl)-1-azabicyclo[2.2.2]oct-3-yl)benzofuran-2-carboxamide or a pharmaceutically acceptable salt thereof.

* * * * *